(12) United States Patent
Särkelä

(10) Patent No.: US 11,793,937 B2
(45) Date of Patent: *Oct. 24, 2023

(54) METHOD AND SYSTEM FOR MONITORING MUSCLE RELAXATION OF A PATIENT AND CORRESPONDING PATIENT CARE SYSTEM

(71) Applicant: GE Precision Healthcare LLC, Wauwatosa, WI (US)

(72) Inventor: Mika Olli Kristian Särkelä, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 650 days.

This patent is subject to a terminal disclaimer.

(21) Appl. No.: 16/829,991

(22) Filed: Mar. 25, 2020

(65) Prior Publication Data

US 2021/0299351 A1    Sep. 30, 2021

(51) Int. Cl.
*A61B 5/11* (2006.01)
*A61B 5/369* (2021.01)
*A61M 5/172* (2006.01)

(52) U.S. Cl.
CPC ......... *A61M 5/1723* (2013.01); *A61B 5/1106* (2013.01); *A61B 5/369* (2021.01); *A61M 2230/08* (2013.01); *A61M 2230/10* (2013.01)

(58) Field of Classification Search
None
See application file for complete search history.

(56) References Cited

U.S. PATENT DOCUMENTS

| | | | |
|---|---|---|---|
| 6,801,803 B2 | 10/2004 | Viertiö-Oja | |
| 7,169,125 B2* | 1/2007 | Jansen | A61M 5/1723 604/66 |
| 7,805,187 B2 | 9/2010 | Särkelä et al. | |
| 7,925,338 B2 | 4/2011 | Huiku | |
| 9,649,063 B2 | 5/2017 | Kokko | |
| 2004/0068229 A1* | 4/2004 | Jansen | G16H 20/17 604/154 |
| 2006/0004296 A1* | 1/2006 | Huiku | A61B 5/4035 600/521 |
| 2008/0097167 A1 | 4/2008 | Yudkovitch et al. | |
| 2009/0275853 A1 | 11/2009 | Särkelä et al. | |
| 2019/0357810 A1* | 11/2019 | Spoof | A61B 5/4519 |

* cited by examiner

*Primary Examiner* — Catherine M Voorhees
*Assistant Examiner* — Elizabeth K So

(57) ABSTRACT

A method of monitoring depth of muscle relaxation of a patient includes determining a sedative drug effect of one or more sedative drugs on a patient based on at least one of drug delivery information and measured nervous system information. The sedative drug effect is then compared to a sedation criterion and, if the sedative drug effect fulfills the sedation criterion, then a neuromuscular transmission (NMT) monitor is controlled to apply a series of stimulation to a nerve of a patient and muscle responses of the patient are measured to obtain an NMT baseline. A neuromuscular blocking agent (NMBA) notice is then generated on a user interface after obtaining the NMT baseline.

13 Claims, 8 Drawing Sheets

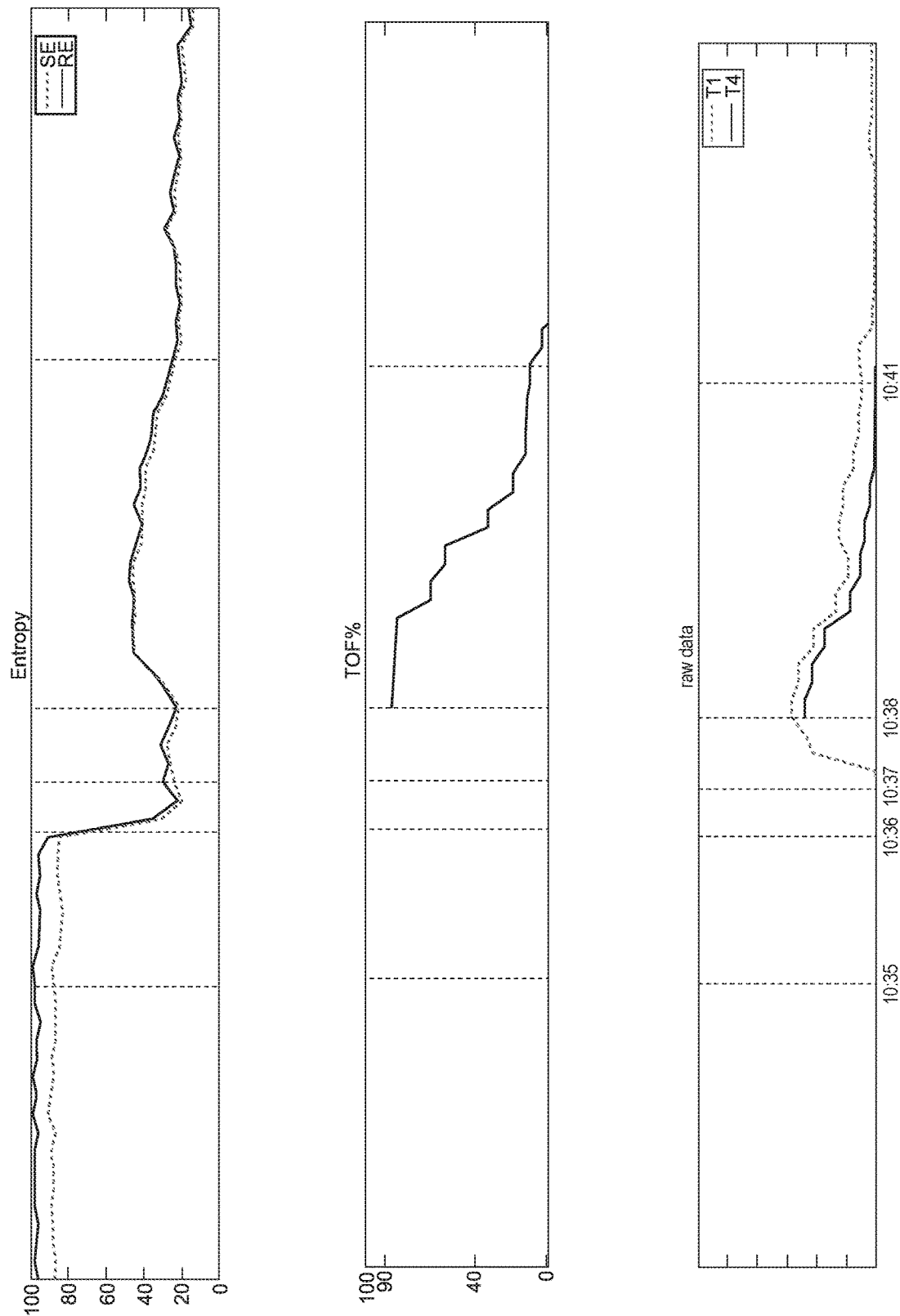

ND SYSTEM FOR MONITORING
METHOD AND SYSTEM FOR MONITORING MUSCLE RELAXATION OF A PATIENT AND CORRESPONDING PATIENT CARE SYSTEM

BACKGROUND

The present disclosure generally relates to medical patient monitoring and controlling patient relaxation levels during anesthesia delivery, and more particularly to systems and methods for monitoring neuromuscular transmission to gauge depth of muscle relaxation of a patient and for controlling neuromuscular blocking agent delivery based thereon.

Neuromuscular transmission (NMT) is the transfer of an impulse between a nerve and a muscle in the neuromuscular junction. NMT may be blocked in a patient undergoing a surgical procedure, for example, by neuromuscular blocking agents/drugs, which may cause transient muscle paralysis and prevent the patient from moving and breathing spontaneously.

Muscle relaxation is used during general anesthesia to enable endotracheal intubation and to provide the surgeon with optimal working conditions. The level of neuromuscular block may be monitored to ensure appropriate block is provided before and during the given procedure and/or to determine when the patient can be safely extubated. At the end of a surgical procedure, the level of NMT is used to determine when the patient can be extubated. Patient sedative state is also monitored throughout anesthesia administration.

Electroencephalography (EEG) is a well-established method for assessing nervous system activity, including brain activity. When measurement electrodes are attached above or within the cerebral cortex, the weak biopotential signals generated in the pyramid cells of the cortex may be recorded and analyzed. Processed EEG signals may be used for objective quantification of the amount and type of brain activity for the purpose of determining the level of consciousness of a patient. Utilization of an EEG signal, for example, allows the automatic detection of the alertness of an individual, i.e. if he or she is aware or unconscious—and for measuring the depth of unconsciousness induced by anesthesia during surgery. Several different analytical and physiological measurement tools are available for determining patient sedative state, or depth of unconsciousness, which may be based on measuring nervous system activity, such as central nervous system activity with EEG or autonomous nervous system activity with heart rate variability (HRV), for example; or may rely on one or more modeling tools well-known in the art for modeling patient sedative state based on drug delivery information and patient demographic information, such as height, weight, etc. Well-known EEG-based tools for assessing patient-sedative state based on a processed EEG signal include Entropy® introduced by General Electric company of Boston, Mass., Bispectral Index™ (BIS) introduced by Medtronic plc, Dublin, Ireland, and Patient State Index (PSi) introduced by Masimo Corporation, Irvine, Calif. Entropy and BIS, as well as other EEG-based methods for measuring depth of sedation, are well-known in the relevant art, such as described at U.S. Pat. Nos. 6,801,803, 7,805,187, and 2009/0275853, to name a few.

Drug modeling, such as pharmacokinetic and pharmacodynamic (PK/PD) drug modeling, are used as an alternative or in addition to the EEG-based sedative state assessment. In this context, sedative drug means any drug that may depress central nervous system activity, such as propofol, sevoflurane, midazolam, fentanyl or dexmedetomidine and sedative drug effect means the effect the drug causes to the patient. The sedative drug effect can be based on the measured physiological information or the drug-delivery information that is either measured or known by other means or modeled. The sedative drug effect can also a combinatory information based on one or more of the above-mentioned information sources. For example, PK/PD models are well known in the relevant art, including their use alone and/or with EEG-based sedative state measurement tools, and exemplary embodiments are described, for example, in U.S. Pat. Nos. 7,925,338, 9,649,063, and 2008/0097167, to provide a few examples.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of monitoring depth of muscle relaxation of a patient includes determining a sedative drug effect of one or more sedative drugs on a patient based on at least one of drug delivery information and measured nervous system information. The sedative drug effect is then compared to a sedation criterion and, if the sedative drug effect fulfills the sedation criterion, then a neuromuscular transmission (NMT) monitor is controlled to apply a series of stimulation to a nerve of a patient and muscle responses of the patient are measured to obtain an NMT baseline. A neuromuscular blocking agent (NMBA) notice is then generated on a user interface after obtaining the NMT baseline.

One embodiment of the patient care system includes an electroencephalograph (EEG) monitor configured to measure EEG potentials from a patient and generate EEG information to indicate nervous system activity, and an NMT monitor configured to measure a depth of muscle relaxation of the patient. A controller is configured to determine a sedative drug effect on the patient based on the EEG information, compare the sedative drug effect against a sedation criterion, and the automatically obtain an NMT baseline with the NMT monitor once the sedative drug effect fulfills the sedation criterion. An NMBA notice is then generated after obtaining the NMT baseline.

Another embodiment of a patient care system includes an EEG monitor configured to measure EEG potentials from a patient and generate EEG information, an NMT monitor configured to measure a depth of muscle relaxation of the patient, and an infusion pump configured to deliver neuromuscular blocking agent (NMBA) to the patient. A controller is configured to determine a sedative drug effect on the patient based on the EEG information and to automatically operate the NMT monitor to periodically obtain an NMT measurement from the patient. The sedative drug effect and the NMT measurement are compared, such as comparing the values to respective criteria indicating a particular level of consciousness and relaxation, respectively. The infusion pump is controlled to deliver NMBA to the patient based on the results of the comparison.

Various other features, objects, and advantages of the invention will be made apparent from the following description taken together with the drawings.

BRIEF DESCRIPTION OF THE DRAWINGS

The present disclosure is described with reference to the following Figures.

FIGS. 3A-3B are graphs of simultaneous Entropy and NMT recordings.

DETAILED DESCRIPTION

Figure 1A:
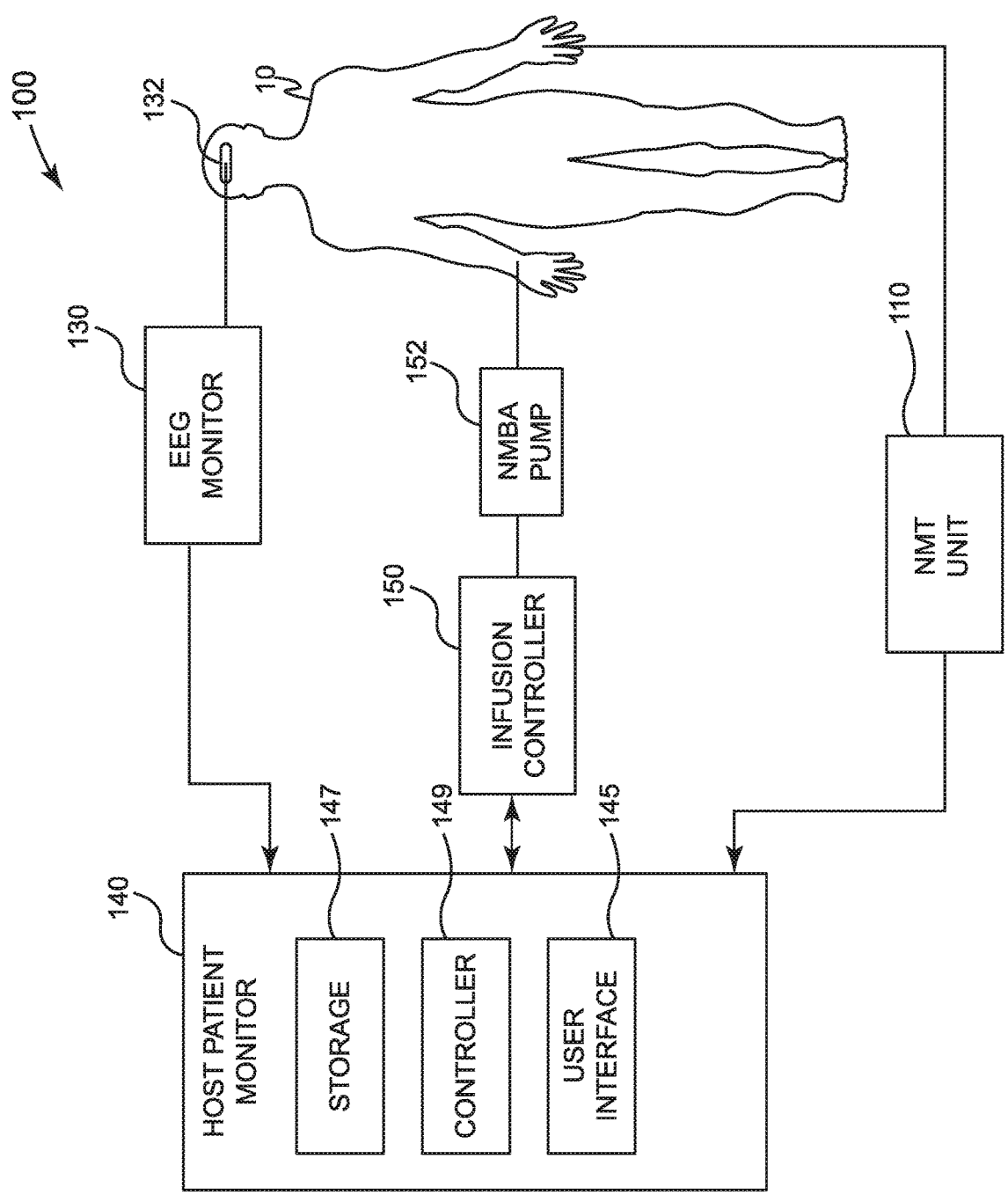
FIGS. 1A-1B Depict exemplary patient care systems providing muscle relaxation monitoring and neuromuscular blocking agent control according to embodiments of the present disclosure.

Neuromuscular transmission (NMT) is the transfer of an impulse between a nerve and a muscle in the neuromuscular junction. NMT may be blocked by neuromuscular blocking agents/drugs, which may cause transient muscle paralysis and prevent the patient from moving and breathing spontaneously. Additionally, muscle relaxation may be used during general anesthesia to enable intubation of an endotracheal tube and to provide the surgeon with optimal working conditions. At the end of a surgical procedure, the neuromuscular block is reversed or allowed to wear off such that neuromuscular activity returns and the patient is able to breathe unassisted before the removal of an endotracheal tube (i.e. extubation). Thus appropriate assessment of the degree of NMT block may be used for ensuring proper timing of extubation and of guiding intraoperative administration of neuromuscular blocking agents to maintain a desired degree of intraoperative neuromuscular block.

An NMT monitor may be used to monitor muscle response to electrical stimulation of a motor nerve (e.g. ulnar nerve). For example, an electrical stimulus may be provided by the stimulus generator at the ulnar nerve near the wrist and the response of the muscle near the thumb, adductor pollicis, may be monitored. In clinical settings, a nerve stimulator is attached to on top of a motor nerve of the patient and an electrical stimulation current is applied to the patient before induction of anesthesia or at least prior to administration of a neuromuscular blocking agent.

The evoked muscle responses may then be monitored through various means, such as measurement of electrical response of the muscle via electromyography (EMG). The measured muscle responses are reviewed in order to gauge the level of muscle relaxation of the patient. In EMG-based NMT measurement modality, multiple electrodes may be used to record the compound muscle action potential evoked by the stimulus. According to embodiments disclosed herein, neuromuscular transmission monitoring may be performed by measuring the electrical potentials at the muscle via an electromyography (EMG) sensor receiving physiologic potentials captured by EMG electrodes, in response to an electric stimulation of a motor nerve. An example of a neuromuscular transmission monitoring system configured to monitor depth of patient relaxation is provided in FIG. 1. The NMT monitoring system may include one or more electrodes which detect electrical activity of a muscle (referred to as EMG electrodes) in response to nerve stimulation, and a nerve stimulator. The NMT monitoring system of FIG. 1 also includes a computing system including instructions to carry out one or more control routines for determining a muscle response baseline, such as maximal muscle response, as well as monitoring neuromuscular block in patients during surgery and post-surgery during recovery.

In addition to EMG-based NMT measurement modality, other modalities exist and may be employed in conjunction with the disclosed method and system for monitoring depth of muscle relaxation. Mechanomyography (MMG) measures the force of thumb bending utilizing a force transducer and is typically assisted with a preload. Acceleromyography (AMG) may use accelerometer for estimating thumb acceleration as a response to stimulus. Still one modality is kinemyography (KMG) which utilizes piezoelectric sensor for measuring thumb bending as a response to stimulus (e.g., via mechano-sensing arrangement 114). Phonomyography (PMG) measures sounds generated by the muscle contraction. As will be evident to a person having ordinary skill in the art reviewing this disclosure, the inventive methods and systems described herein are applicable in all neuromuscular transmission (NMT) measurement modalities.

An NMT baseline is a prerequisite for the reliable NMT monitoring. Reference value is determined based on the muscle responses recorded before the muscle relaxant administration by the NMT monitor and it may be used to normalize the muscle responses once the muscle relaxant is administered. In one embodiment, maximal stimulus current is defined with a sweep of increasing stimulation currents and measuring subsequent muscle responses. The point where strength of muscle response is not increased anymore by the increasing stimulus current is defined as the maximal stimulus current. For example, giving 20 mA stimulus and measuring response, 25 mA stimulus and measurement, 30 mA etc. When the measured response reaches a plateau, the maximal stimulus current is obtained. Supramaximal stimulus current may be defined as the current 15-20% higher than the maximal stimulus current. Once the NMT baseline is established, NMT monitoring can proceed. As examples, the NMT baseline may include (a) a reference muscle response, (b) a stimulus current determination, (c) both a and b, (d) the first TOF % value, etc.

Establishment of the NMT baseline must be established before neuromuscular blocking agent (NMBA) is administered to the patient. Clinicians avoid starting NMT monitoring on conscious patients because it causes extra stress to a typically already anxious patient. Although NMT measurement is not necessarily painful, it can be somewhat startling and uncomfortable for a patient. In addition, NMT monitoring may be corrupted by the voluntary movements of awake patient. Thus, NMT monitoring and establishment of the NMT baseline is typically started after some amount of sedation has been administered to the patient so as to reduce their level of consciousness.

In current systems, the startup of NMT monitoring is performed manually by a clinician, such as by pressing a button or otherwise instructing NMT start at the NMT monitor or at a host patient monitor in control communication with the NMT monitor. Currently, the start of NMT monitoring is identified and defined subjectively, which is often dictated by the work flow of the clinician and other factors. This leads to mistiming of NMT monitoring start. When NMT monitoring is started too early, it causes unnecessary patient discomfort and stress. Where NMT is started too late, administration of NMBA to the patient is possibly already started and the NMT baseline cannot be obtained anymore. In other embodiments, NMBA administration is given too early where the patient has not reached a sufficiently deep sedative state and thus is still awake. This can expose the patient to a traumatic experience where they lose all muscle control and the ability to breathe autonomously, but are still awake and conscious of the experience. In current systems, proper timing of NMBA administration is defined subjectively by interpreting patient behavior and responsiveness, which can lead to improper timing of patient relaxation.

In view of the foregoing problems and challenges in the relevant art, the present inventor developed the disclosed patient care system and method which integrates NMT monitoring and patient sedation monitoring into a system for automatically advising and or controlling NMBA administration so as to avoid improper timing of NMT monitoring and/or NMBA administration. In certain embodiments, the disclosed patient care system may provide continued NMT monitoring and NMBA guidance or control throughout the anesthesia administration and surgical procedure to continually assess the appropriateness of the patient's relaxation level, such as based on a comparison to the sedative drug effect of the patient and the stage of the procedure.

In one embodiment, the sedative drug effect on a patient is monitored at the beginning of anesthesia, and a host patient monitor (or centralized monitoring system) is configured to automatically start NMT monitoring once the patient reaches a moderate sedation level that permits NMT stimulation without stressing or disturbing the patient.

In certain embodiments, ongoing sedative drug effect and NMT monitoring may then be performed and the results compared to provide controlled and consistent NMBA administration and/or an NMBA reversal recommendation notice to a clinician, as appropriate. For example, at the end of a procedure the sedative drug may wear off more quickly than the NMBA. This can lead to a scenario where a patient is awake but cannot move. The disclosed patient care system may be configured to compare a sedative drug effect value, such as an Entropy or BIS value to a recovery criterion and to compare an NMT measurement to a recovery criterion to assess whether the depth of muscle relaxation of the patient is appropriate or is too deep (i.e., the NMT measurement value is too low). If the patient's sedative state is comparatively shallower than their state of relaxation, and thus the depth of muscle relaxation of the patient is too deep, then the system may be configured to provide an alert to a clinician recommending administration of an NMBA reversal agent.

Figure 1B:
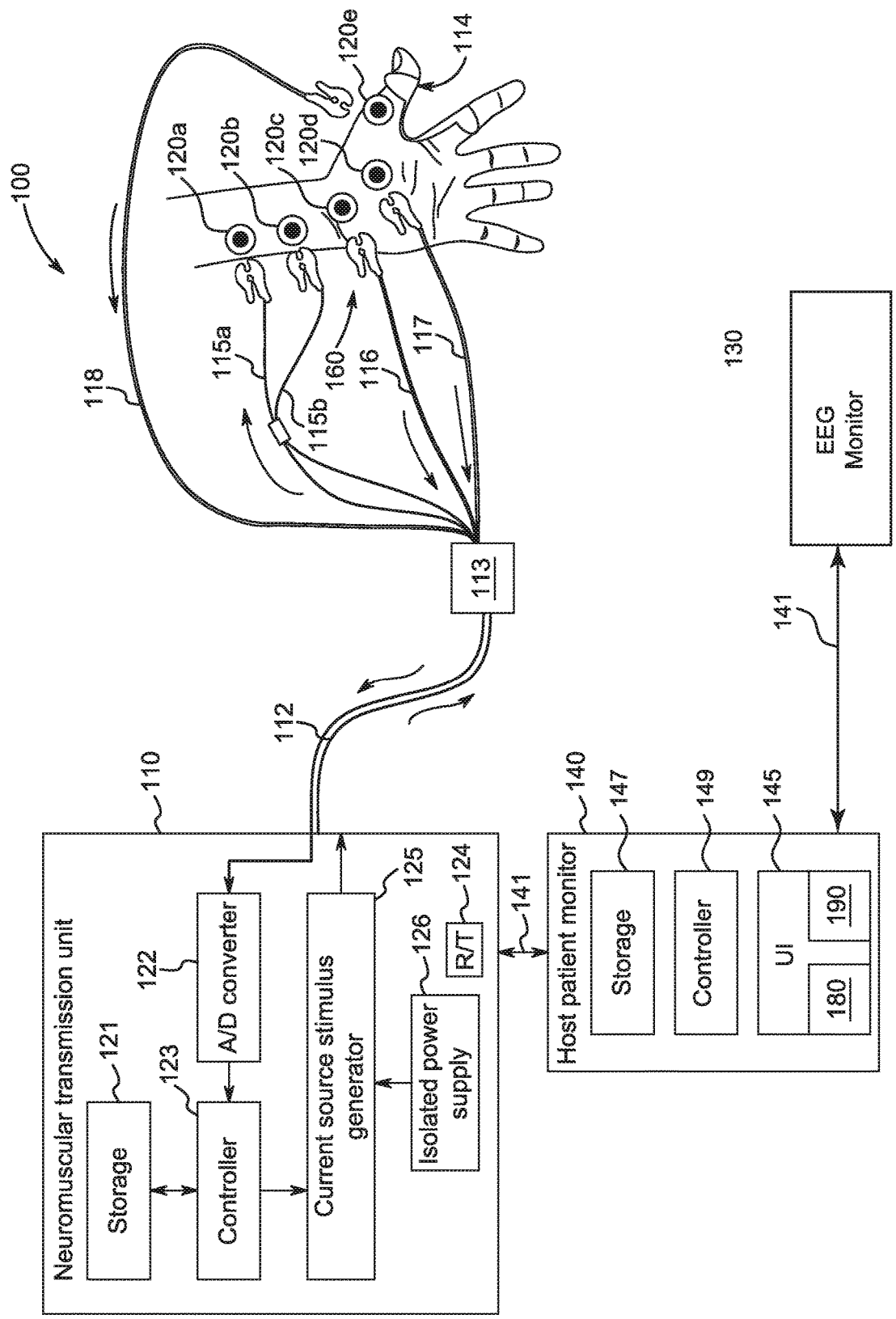

FIGS. 1A-1B illustrates an exemplary patient care system 100 that includes NMT monitoring and EEG monitoring. The NMT monitor is configured to monitor neuromuscular activity and depth of muscle relaxation, such as via EMG or KMG techniques. The NMT unit 110, which in some embodiments may be an NMT transmission unit configured to control and transmit stimulation, is communicatively coupled to a host patient monitor 140 via a communication link 141. Similarly, the EEG monitor 130 is configured to record EEG potentials from the patient 10 via one or more EEG electrodes 132, such as an electrode strip configured to attach to the patient's forehead, and to communicate with the host patient monitor via communication link 141. In various embodiments the communication link 141 may be a wired or wireless communication means. In a wireless embodiment, the NMT unit and/or the EEG monitor may have a wireless receiver/transmitter 124 (see FIG. 1A) configured to wirelessly communicate with the host patient monitor 140. In such an embodiment, the communication link 141 being a wireless communication link, may be via any of various wireless protocols, such as Bluetooth, Bluetooth low energy (BLE), ZigBee, or may be via the wireless medical telemetry service (WMTS), to provide just a few examples.

Referring also to FIG. 1B, the NMT unit 110 is connected to a plurality of neurostimulators 115a and 115b for providing stimulation output (e.g., electrical stimuli) of varying type and frequency to the patient and at least one input connected to one or more transducers for monitoring the evoked muscle response in response to the electrical stimuli provided by the neurostimulators. The transducers include an EMG sensor 160 consisting of a plurality of electrodes 120c-120e for measuring the action potential of muscle contraction in response to nerve stimulation. The signals detected by the electrodes may then be converted into digital signals by the A/D converter 122 of neuromuscular transmission unit 10.

In one embodiment illustrated in FIG. 1B, the EMG muscle response signals received from EMG sensor 160 may be sent to NMT unit 110 via main connector 113 and cable 112. In one example muscle response signals from EMG sensor 160 sensor are fed into a signal scaling and filtering circuit (not shown). After scaling the signal and filtering noise, the signal may be converted from an analog signal to a digital signal in analog-to-digital (A/D) converter 122 and sent to a controller 123 for processing. Further, the muscle signal response signals may also be amplified via an amplifier (not shown) before being transmitted into the A/D converter 122. The controller 123, or processing unit, is connected to a storage device 121 and once the signals are processed, the signal data may be displayed on the display unit 190 of the host patient monitor 140. In one example, the processed signals may be transmitted to the host patient monitor 140 and displayed on the display unit 190 in real-time.

In the depicted example, neurostimulators 115a and 115b are connected to stimulating electrodes 120a and 120b, respectively, which may apply an electrical stimulus to the patient's ulnar nerve at a pre-determined time interval. The amount of electrical stimulation provided to the neurostimulators is controlled by a current stimulus generator which receives commands signals from controller 123. In one embodiment, controller 123 of the NMT unit 110 is linked to a user interface 145, such as on the host patient monitor display unit 190 and buttons/knobs 180. The type and frequency of the stimulation output may be adjusted by the user via pressing buttons or knobs 180 on the patient host monitor 140. In other embodiments, the type and frequency may be automatically selected or controlled by the controller 149 based on various factors. In one example, neurostimulators 115a and 115b may be two wires of positive and negative charges, which may be attached by alligator clips or other attachment means to stimulating electrodes 120a and 120b on the skin of the patient's forearm.

A power supply (not shown) may supply electricity to an isolated power supply 126 which in turn provides power to current source stimulus generator 125. The controller 123 may be connected to the current source stimulus generator 125 to adjust the amount of electric current provided to the neurostimulators 115a-115b. The current stimulus generator 125 may generate different types of neurostimulation including train-of-four (TOF), single twitch (ST), double burst (DBS), post-tetanic count (PTC), current range (e.g., 1-70 mA with 1 mA steps), pulse width/frequency (e.g., 100, 200, 300 μs, or 1 Hz, 2 Hz, etc.). Further, the types of neurostimulation may be chosen via a manual or an automatic stimulating mode.

If an automatic neurostimulation mode is chosen, controller 123 of NMT unit 110 may select a first neurostimulation type as its default setting, such as TOF stimulation, and based on the muscle response signals received from the EMG electrodes the controller reports the muscle response signals to the user by displaying graphs and numbers (e.g., via display unit 190 of host patient monitor 140). The display unit 190 may display the muscle response data/ information to the user and may also include alarm signals and notices for alerting the user.

Additionally, NMT unit 110 may be connected to a host patient monitor 140 through a communication link 141. Host patient monitor 140 may include storage 147, controller 149 and user interface (UI) 145. Storage device 147 may have similar functions as storage device 121 to store stimulus information and or baseline information as well as relevant criteria and patient information. User interface (UI) 145 include control buttons/knobs 180 and display unit 190. The control buttons and inputs of UI 145 may be configured to allow for user input. The display unit 190 may be configured to receive touch input from a user.

One preferred neuromuscular stimulating output of the present disclosure is a train-of-four (TOF). In one example, TOF may typically use four brief (between 100 and 300 μs) current pulses (generally less than 70 mA) at 2 Hz, periodically conducted every 10 to 20 seconds as electrostimulation. The resulting twitches (i.e. muscle responses) may be measured and quantified for electromyography response via EMG sensor—i.e., the TOF response. In one embodiment, the TOF response is determined by comparing the first twitch (referred to as the T1 twitch) and the last twitch (referred to as the T4 twitch). The ratio of the last twitch to the first twitch (referred to as TOF ratio) may provide an estimate of the level of neuromuscular blockade (e.g., depth of relaxation) experienced by the patient. The TOF ratio may range from 0 to 100%, for example, in addition to the TOF ratio, another ratio that can be calculated during TOF stimulation is referred to as TO2. TO2 is the ratio of the second twitch (T2) to the first twitch (T1) in the train-of-four stimulation pulses. Other examples of quantified NMT parameters are TOF count, which is number of identified TOF responses after TOF stimulus, and T1%, which is the ratio of the current T1 twitch to the baseline T1 twitch recorded before the administration of neuromuscular blocking agent. The electrical TOF stimuli series may be spaced by ten or more seconds (generally 20 seconds is used to provide a margin of safety) to give a rest period for full restoration of steady-state conditions, as faster stimulation may result in smaller evoked responses. TOF stimulation is the most commonly used technique for monitoring the neuromuscular blockade during moderate (TOF count 1-3), shallow (TOF ratio <40%), and minimal block (TOF ratio 40-90%) as well as in patients that are recovering from neuromuscular block; however, other stimulation methods may be utilized and are within the scope of the present disclosure.

Figure 2:
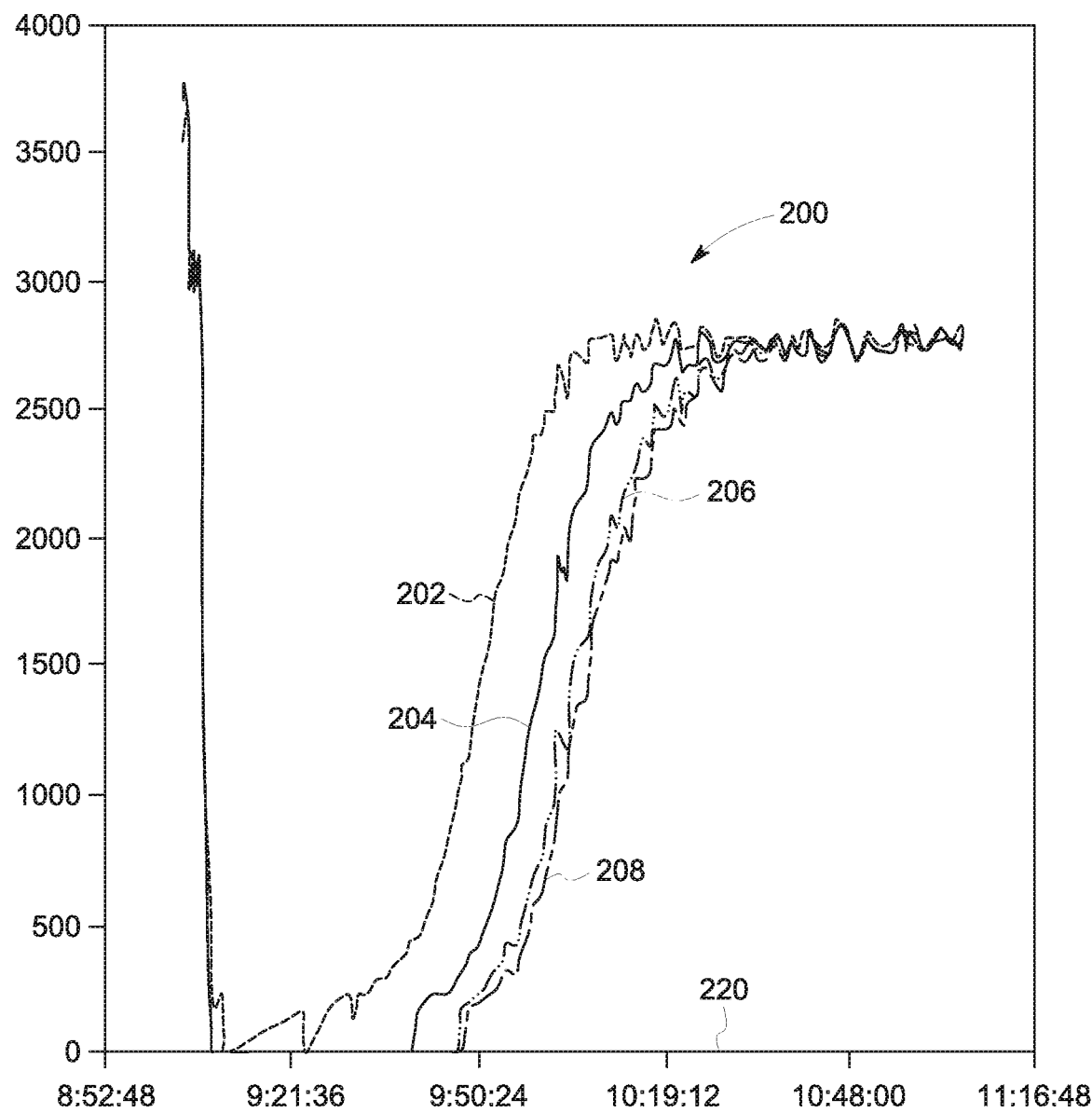
FIG. 2 is a graph showing muscle responses to a series of stimulations, and particularly a train-of-four (TOF) stimulation.

FIG. 2 illustrates the EMG responses to each of the four pulses of a TOF stimulation over a measurement period set forth on this horizontal axis of the graph. The first twitch, referred to as the T1 twitch, is graphically illustrated by trace 202 in the graph 200. The second twitch, referred to as the T2 twitch, is shown by trace 204 while the third twitch, T3, is illustrated by trace 206. The last and final twitch, referred to as the T4 twitch, is shown by trace 208. As can be seen by the combined graph 200 of FIG. 2, the T1 trace 202 begins to be detected at the earliest point in time since the T1 twitch is in response to the first stimulation of the TOF simulation sequence. The T2, T3, and T4 twitches begin to be detected at a time slightly delayed from the detection of the T1 twitch, as is well known for a patient recovering from the neuromuscular blocking agent.

Figure 3A:
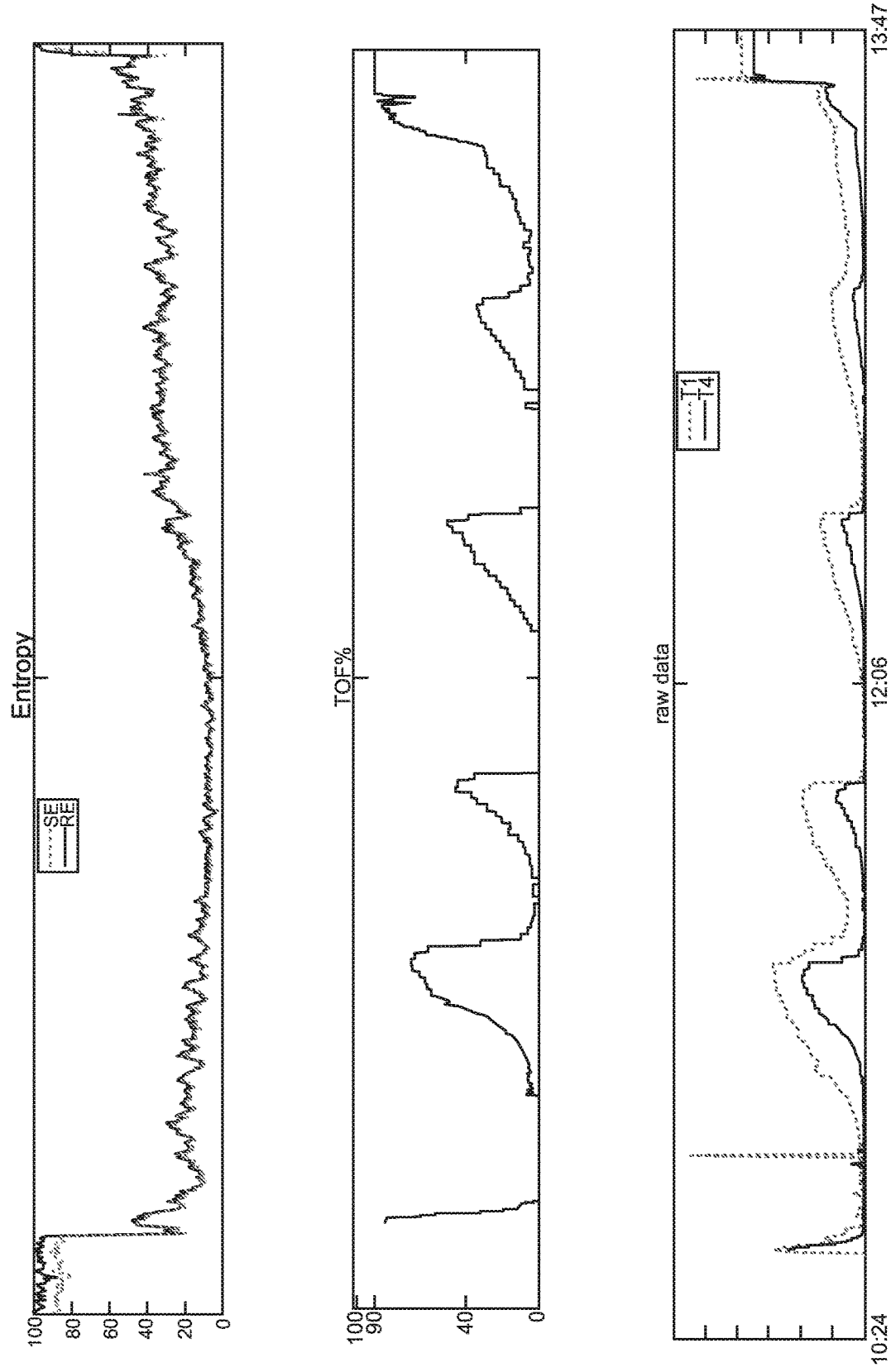

FIG. 3A illustrates an exemplary recording of simultaneous Entropy and NMT monitoring in operating room for anesthesia and surgery. The top graph presents Entropy parameters, including Response Entropy (RE) and State Entropy (SE). Response Entropy range is 0-100, whereas State Entropy range is 0-91. High entropy values (<80) indicate awake patient with zero or minimal sedative drug effect. Entropy range 60-80 corresponds to moderate sedation, while Entropy range 40-60 is typically maintained during general anesthesia. In this context, Entropy range below 60 refers to deep sedation. The same is also true for Bispectral Index (BIS). With Patient State Index (PSi), the correspondence between sedation levels and index values are slightly different and the index value of 50 may be used as a limit, or criterion, between moderate and deep sedation. While a patient is being prepared for anesthesia, entropy monitoring is started and both Entropy parameters are typically above 80. In this example, when sedative drug(s) take effect, both Entropy parameters drop rapidly. During surgery sedative drug is administered for keeping Entropy parameters below 60. After anesthesia, Entropy parameters increase to above 80.

FIG. 3B highlights the time-section of simultaneous Entropy and NMT recordings around the time of anesthesia induction, including NMT baseline establishment and initial administration of NMBA. The middle graph presents TOF ratio over time. The first TOF ratio value is obtained after the NMT monitoring is started and it is over 80% in this case. As this example demonstrates, measured TOF ratio of unrelaxed patient is not always 100%. Evoked thumb movement between four successive stimuli may vary and the mechanic response for later stimuli may be different than for the first response. That may occur especially with AMG and KMG modalities, underscoring the importance of baseline evaluation. The NMT baseline is established and, after the first bolus of neuromuscular blocking agent is administered, the TOF ratio then declines to the zero level.

In FIG. 3A, middle graph, here the neuromuscular blocking agent is administered in boluses and the drug effect starts to wear off quite rapidly, which can be seen from the subsequent rise in the TOF ratio. As can be interpreted based on the TOF ratio curve, four additional NMBA boluses are administered during the operation period depicted in the graph. At the end of operation, TOF ratio reaches the 90% level, which is the current consensus guideline limit for the safe extubation. The bottom graph presents the T1 and T4 twitches. As seen, some artefactual twitch values are filtered away and they do not become apparent on the TOF ratio.

Referring again to FIG. 3B, the first vertical line at 10:35 represents the start of sedative drug (propofol) infusion. The second vertical line at 10:36 represents the time point where the patient does not respond to command anymore. This time point is typically interpreted as the transition to unconsciousness. As seen, this time point occurs at the same time as the drop of Entropy parameters. The third vertical line at 10:37 represents the start of NMT measurement. At that time, NMT monitor starts to stimulate patient with alternating stimulus currents and patient response to each stimulus is measured in the form of T1. Once the response to the increasing stimulus current does not change anymore, patient-specific stimulus current is determined, and that stimulus current is preferably used during the whole procedure. In addition, baseline T1 twitch for patient-specific stimulus current is recorded and stored. The fourth vertical line at 10:38 represents the time point where the start-up of NMT monitoring is complete and NMBA administration is safe—i.e., 1) the risk for patient awareness is low and 2) NMT measurement values are reliable.

A first bolus of neuromuscular blocking agent is administered soon after and subsequent decline in TOF ratio and in T1 and T4 twitches is observable. The first bolus is typically administered for facilitating patient intubation, as in this example. Intubation often increases Entropy parameter values, as in this example, but if they remain below 60 the risk for patient awareness is low. The fifth vertical line in FIG. 3B. at 10:41 marks the time point when the endotracheal tube is in place.

The disclosed method and system are configured to automatically begin NMT monitoring and to obtain an NMT baseline, and then to generate an NMBA notice on the user interface, such as on the user interface 145 of the host patient monitor 140 and/or on a user interface associated with an anesthesia machine. In one embodiment, the controller 149 of the patient monitor 140 is configured to assess the sedative drug effect of the patient based on measured nervous system information, such as EEG information, and or drug delivery information and to compare the sedative drug effect to a sedation criterion to assess the patient's sedation level. In one embodiment, the sedation criterion is the first sedation criterion representing a first sedative state, the first sedative state corresponding to moderate sedation level or deeper and after the sedative drug effect indicates that the patient has reached the first sedative state, the NMT unit 110 is operated to obtain the NMT baseline, as is described herein. In certain embodiments, the patient monitor 140 may be configured to continually monitor the sedative drug effect of the patient until the sedative drug effect reaches a second sedative criterion representing a second sedative state, the second sedative state corresponding to equivalent or deeper sedation than the first sedative state, at which point the NMBA notice may be generated.

In certain embodiments, the NMBA notice may be a notice to a clinician that it is safe and appropriate to begin NMBA administration. In other embodiments, the patient care system 100 may be configured to automatically initiate NMBA administration to the patient. In certain embodiments, the host patient monitor 140 may be communicatively connected to an infusion controller 150 controlling one or more infusion pumps, including an NMBA pump 152. In one embodiment, the controller 149 of the host patient monitor 140 is configured to determine when initiation of NMBA is appropriate and to automatically begin NMBA administration once an NMT baseline is obtained and the sedative drug effect fulfills a sedation criterion indicating sufficient sedation level. In certain embodiments, the controller 149 may be configured to also automatically begin NMT monitoring and obtaining an NMT baseline based on sedative drug effect monitoring, such as when the sedative drug effect fulfills a first sedation criterion representing a first sedative state. For example, once EEG monitoring has been started, the monitor may prompt user to confirm, whether the host monitor 140 will start NMT monitoring automatically or if user would like to use manual NMT start-up, as it is the current practice. Various examples of control methods are described herein.

Figure 4:
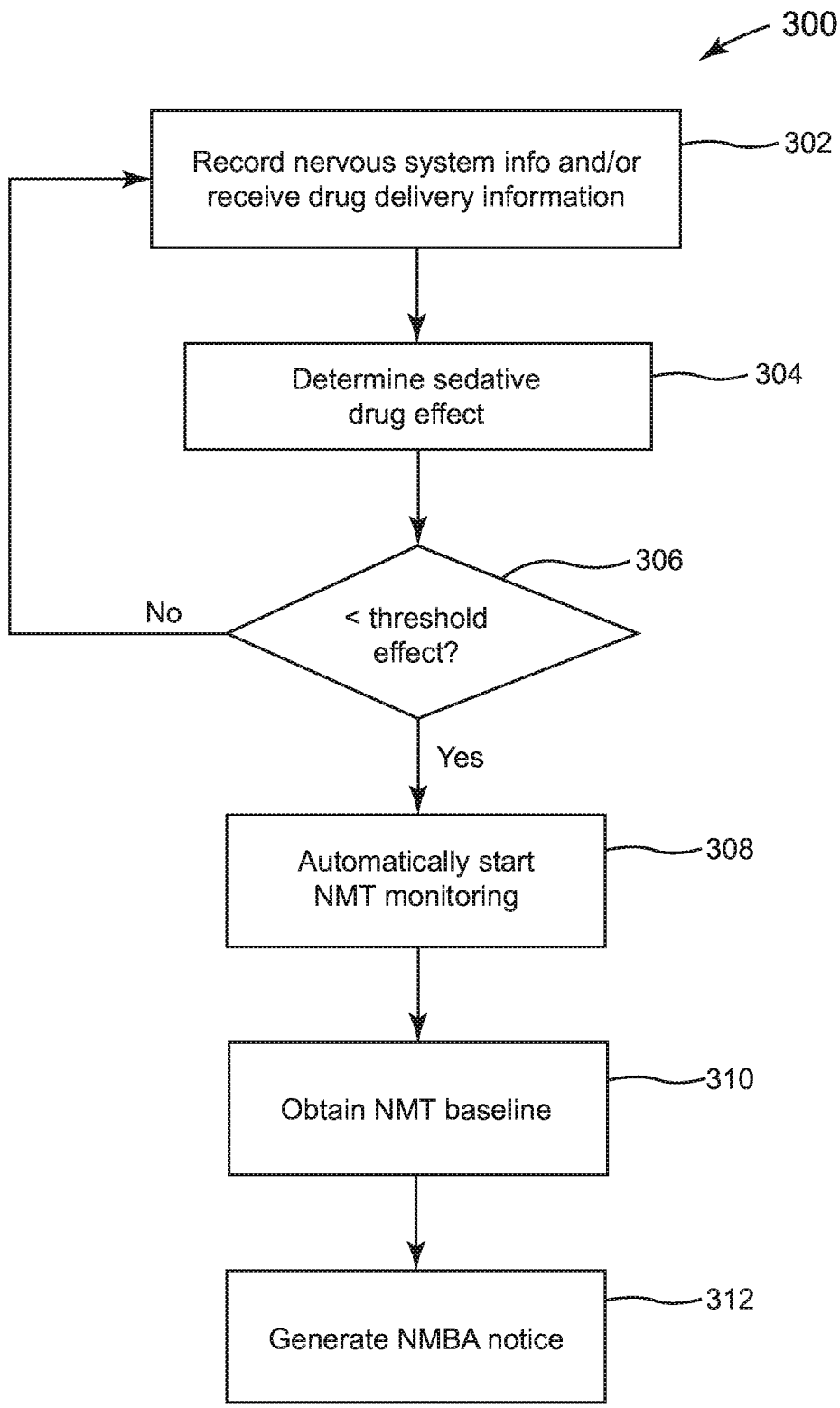
FIG. 4-6 depict embodiments, or portions thereof, of methods of monitoring depth of muscle relaxation of a patient in accordance with the present disclosure.
Figure 5:
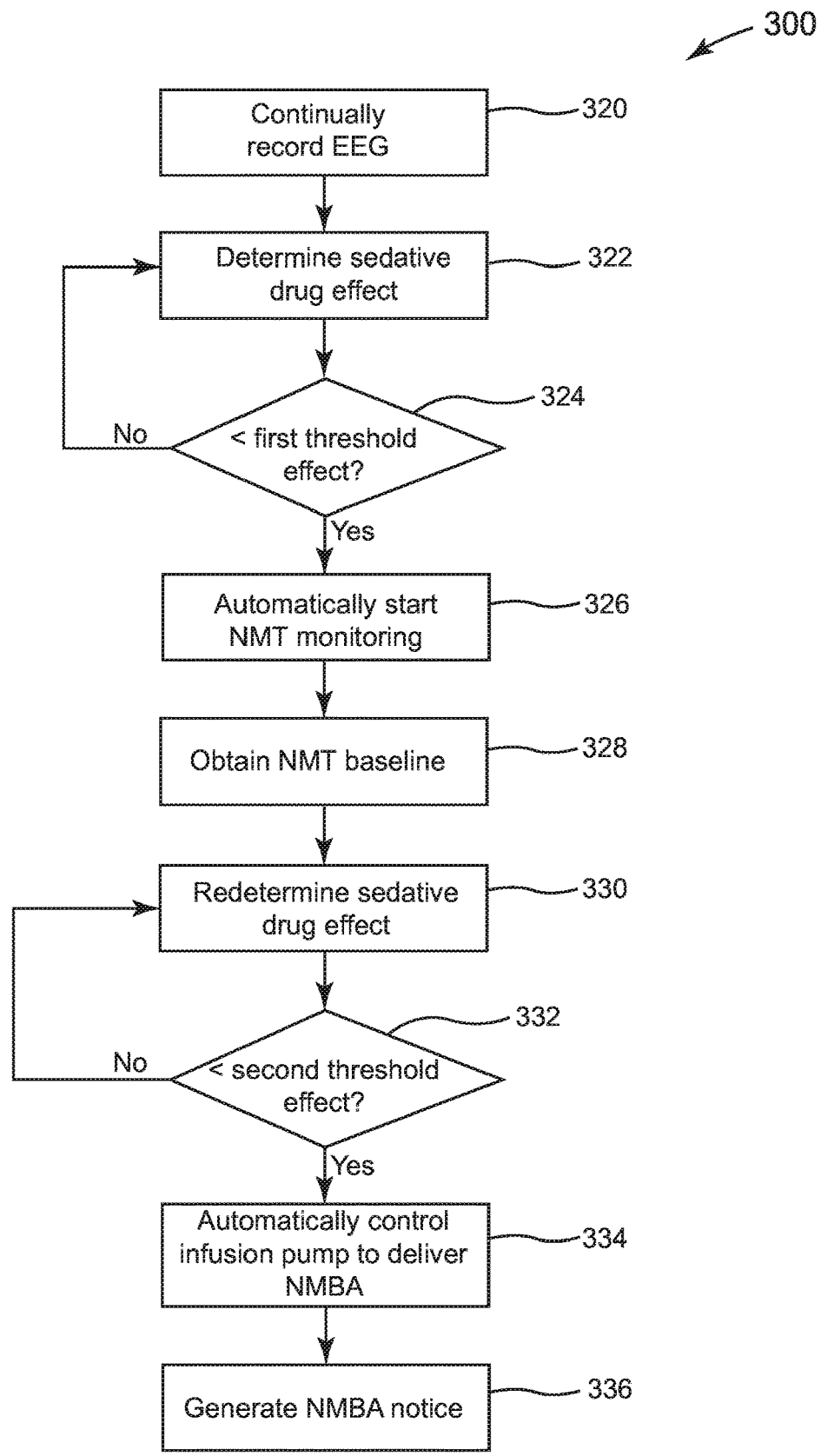
Figure 6:
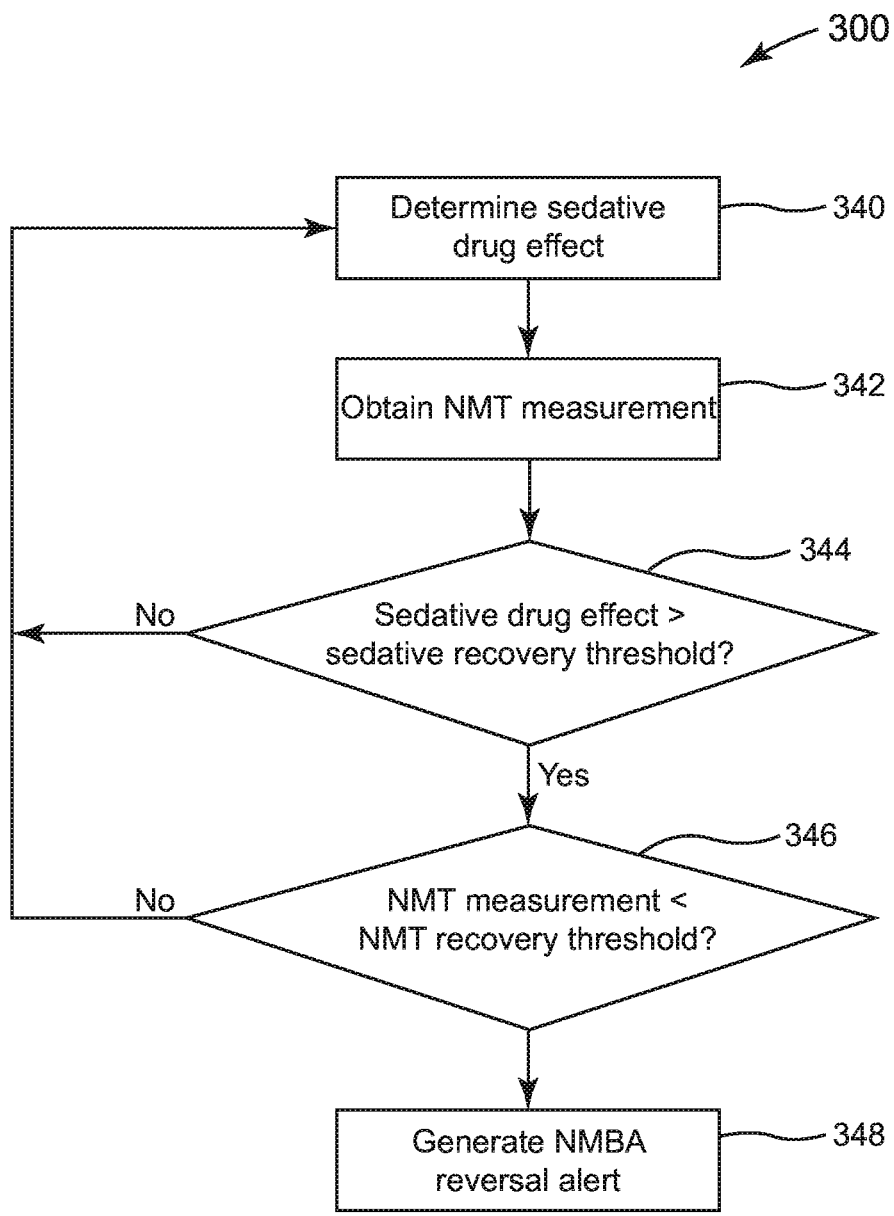

FIGS. 4-6 depict embodiments of methods 300 of monitoring depth of muscle relaxation of a patient 10. In the embodiment of FIG. 4, measured nervous system information, such as EEG information, is recorded and/or drug delivery information is received at step 302. The sedative drug effect of the patient is determined at step 304 based on the EEG information and/or the drug delivery information. As described herein, EEG-based sedative drug effect values may include, for example, Entropy and BIS. Alternatively or additionally, the sedative drug effect may be a model-based value, such as a PK/PD modeled value. Once the sedative drug effect reaches a threshold at step 306, then NMT monitoring is automatically initiated at step 308, where a series of stimulations are applied to the nerve of the patient and muscle responses are measured so as to obtain an NMT baseline at step 310. Once the sedative drug effect is below (or over, if PK-PD modeled drug concentration estimate is used) at least the first threshold and the patient-specific optimal stimulus current and/or the NMT baseline is established, then an NMBA notice is generated at step 312. In certain embodiments, the NMBA notice may be a notice indicating to a clinician that it is safe to deliver NMBA to the patient and that NMBA administration should be initiated by the clinician.

FIG. 5 depicts an embodiment wherein NMBA administration is automatically performed based on the sedative drug effect and NMT monitoring. An EEG monitor is operated to continually record EEG from the patient at step 320. The sedative drug effect 322 is determined periodically at step 322 based on the EEG information. Once the sedative drug effect reaches a first threshold effect at step 324, then an NMT unit is automatically controlled to start NMT monitoring at step 326. An NMT baseline is established at step 328. The sedative drug effect is periodically determined, or presented at step 330. Once the sedative drug effect reaches a second sedation criterion at step 332, then the infusion pump is automatically controlled at step 334 to deliver NMBA to the patient. An NMBA notice is generated at step 336 to indicate that NMBA is being delivered to the patient. To provide just one example, where sedative drug effect is indicated as State Entropy, the first sedation criterion may be, for example, a State Entropy less than 80 and the second sedation criterion may be, for example, a State Entropy less than 70. In some surgeries, NMBA is delivered on constant infusion rate for providing stable surgical conditions. In this conjunction, trend of the sedative drug effect can be monitored for controlling NMBA infusion. For example, if there the prominent increase on State Entropy trend is detected, for example from State Entropy value of 45 to 65 within 5 minutes (suggesting end of surgery and decrease on sedative drug delivery), NMBA notice may indicate clinician to stop NMBA infusion or NMBA infusion may be halted automatically.

In certain embodiments, NMT monitoring may be conducted throughout the surgical procedure and or at the end of the surgical procedure to assess whether the muscle relaxation of the patient has worn off. In this case, patient is able breath by him/herself and ready for extubation. If the level of muscle relaxation is too deep the NMBA reversal should be administered. In well-known NMT monitoring methods, extubation of the patient occurs when NMT parameter of the patient reaches a recovery threshold at which the neuromuscular blocking has been diminished enough such that the patient can spontaneously breathe. In many monitoring systems, the recovery criterion is based on the TOF ratio. In one example, the NMT recovery criterion may be a TOF ratio of 90%. As can be understood with respect to FIG. 2, the TOF ratio of 90% occurs when the T4 trace 208 begins to closely correspond to the T1 trace 202. In some embodiments, for example in connection with the recording presented in FIG. 3, it may be beneficial to use normalized TOF (nTOF) ratio instead of conventional TOF ratio. In nTOF, the patient baseline TOF measurement is set as 100% and the subsequent TOF measurements are divided with the baseline. Thus, in the example of FIG. 3A the nTOF recovers to value of (90/80) %=113%. In other embodiments, the recovery threshold may be higher or lower, or may be a different value that corresponds with the NMT monitoring method implemented.

In certain embodiments, the NMT measurement may be monitored in conjunction with the sedative drug effect to assess whether the level of muscle relaxation of the patient is too deep compared to the patient's sedative state such that the patient may be recovering consciousness prior to recovering muscle function. In certain embodiments, the system 100, such as the host patient monitor 140, may be configured to receive inputs relating to a stage of the surgical procedure and/or the sedative and relaxation requirements of the procedure. During surgery, neuromuscular blockade and sedation are defined independently. Requirements of surgery define the needed relaxation level, whereas sedation is controlled for keeping patient physiologically stable and unaware of the surroundings. Such control requirements may be inputted by a clinician, such as via the user interface 145, for example.

The sedative drug effect may be compared to a sedation recovery criterion in order to assess the patient's sedative state, and the relative comparison between the sedative drug effect and the sedation recovery criterion may be compared to that of the NMT measurement and the NMT recovery criterion. Namely, if it is determined that the sedative drug effect fulfills the sedation recovery criterion and the NMT measurement do not fulfill the NMT recovery criterion, then it may be determined that NMBA reversal is needed and an NMBA reversal notice, or alert, may be generated on the user interface, such as the user interface 145 of the patient monitor 140, to alert the clinician of the patient's state of relaxation and provide a recommendation to administer NMBA reversal to the patient. To provide just one example, where the sedative drug effect is a State Entropy, the sedation recovery criterion may be, for example, a State Entropy exceeding 80. Where NMT monitoring is train-of-four, the NMT recovery criterion may be a TOF count 4. In other embodiments, the recovery threshold may be a TOF %, such as 40%.

Referring to the example at FIG. 6, the sedative drug effect is determined at step 340, as is described above. The NMT measurement is obtained at step 342. Instruction are executed at step 344 to determine whether the sedative drug effect fulfills the sedation recovery criterion, meaning that minimal sedation is in effect. If not, then the sedative drug effect and NMT monitoring continues as patient recovery process proceeds. Likewise, the NMT measurement is compared to the NMT recovery criterion at step 346 as the patient recovers. Once the sedative drug effect fulfills the sedative recovery criterion, if the NMT measurement remains less than the NMT recovery criterion at step 346, then an NMBA reversal alert is generated to provide an NMBA reversal recommendation.

The sedation criterion, the sedation recovery criterion and the NMT recovery criterion may be based on a current sedative drug effect and NMT measurement values, or may use multiple sedative drug effect and NMT measurement values recorded during the monitoring period. In addition, criteria may also utilize patient demographic data. For example, in one scenario sedation induction may be slower than usual. In this scenario, Entropy values from the time window of the past three minutes can be analyzed and the first sedation criterion would be fulfilled once the three-minute history demonstrates clear downward trend and the current Entropy value is less than 75. Similarly, the second sedation criterion will be fulfilled once the five-minute history demonstrates clear downward trend and the current Entropy value is less than 65. Likewise, NMT recovery criterion may be compared to NMT measurement values of past five minutes. For example, NMT recovery criterion may be fulfilled if the five-minute NMT data demonstrates clear upward trend with a sufficiently steep slope. For example, if TOF ratio has increased from the level of 20% to 50% within the past five minutes, NMT recovery criterion is fulfilled and NMBA reversal is not recommended.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A method of monitoring depth of muscle relaxation of a patient, the method comprising:
   determining a sedative drug effect of one or more sedative drugs on the patient based on at least one of drug delivery information and measured nervous system information;
   comparing the sedative drug effect to a sedation criterion;
   determining that the sedative drug effect fulfills the sedation criterion;
   based on the determining step, automatically controlling a neuromuscular transmission (NMT) monitor to apply a series of stimulations to a nerve of a patient and measuring muscle responses thereto; and
   obtaining an NMT baseline based on the measured muscle responses.

2. The method of claim 1, comprising generating a neuromuscular blocking agent (NMBA) notice on a user interface after obtaining the NMT baseline.

3. The method of claim 2, wherein the NMBA notice is an NMBA safe notice indicating that it is safe to deliver NMBA to the patient.

4. The method of claim 1, wherein the sedation criterion is a first sedation criterion representing a moderate sedative state or deeper and wherein the step of automatically applying the series of stimulations is performed after determining that the sedative drug effect of the patient fulfills the first sedation criterion.

5. The method of claim 4, further comprising:
   monitoring the sedative drug effect of the patient over time;
   comparing the sedative drug effect to a second sedation criterion representing an equivalent or deeper sedative state than the first sedation criterion;
   determining that the sedative drug effect of the patient fulfills the second sedation criterion prior to generating a neuromuscular blocking agent (NMBA) notice on a user interface.

6. The method of claim 5, further comprising, after determining that the sedative drug effect of the patient fulfills the second sedation criterion and after obtaining the NMT baseline, automatically controlling an NMBA delivery device to deliver NMBA to the patient, wherein the NMBA notice is notice that NMBA is being delivered to the patient.

7. The method of claim 1, wherein the sedation criterion represents a deep sedative state and further comprising determining that the sedative drug effect of the patient fulfills the sedation criterion prior to generating a neuromuscular blocking agent (NMBA) notice on a user interface.

8. The method of claim 7, further comprising, after determining that the sedative drug effect of the patient fulfills the sedation criterion and after obtaining patient-specific NMT information, automatically controlling an NMBA delivery device to deliver NMBA to the patient, wherein the NMBA notice indicates that NMBA is being delivered to the patient.

9. The method of claim 1, wherein the sedative drug effect is one of an entropy value determined based on EEG information, a bispectral index value determined based on the EEG information, a patient state index value determined based on the EEG information, and a model-based value determined based on the drug delivery information and patient demographic information.

10. The method of claim 1, wherein the NMT baseline includes at least one of a maximal stimulus current and a supramaximal stimulus current and a reference set of muscle response measurements.

11. The method of claim 1, further comprising:
periodically determining the sedative drug effect of the patient based on the drug delivery information and/or EEG information;
periodically applying the series of stimulations to the nerve of the patient and measuring muscle responses thereto to obtain an NMT measurement; and
comparing the sedative drug effect to the NMT measurement to determine whether the level of muscle relaxation of the patient is too deep.

12. The method of claim 11, wherein comparing the sedative drug effect to the NMT measurement includes:
comparing the sedative drug effect to a sedation recovery criterion;
comparing the NMT measurement to an NMT recovery criterion; and
further comprising, upon determining that the sedative drug effect fulfills the sedation recovery criterion and the NMT measurement do not fulfill the NMT recovery criterion, generating an NMBA reversal notice on a user interface recommending NMBA reversal.

13. A patient care system comprising:
a memory storing instructions;
a processor configured to execute the instructions to:
determine a sedative drug effect of one or more sedative drugs on the patient based on at least one of drug delivery information and measured nervous system information;
compare the sedative drug effect to a sedation criterion;
determine that the sedative drug effect fulfills the sedation criterion;
based on the determining step, automatically control a neuromuscular transmission (NMT) monitor to apply a series of stimulations to a nerve of a patient and measuring muscle responses thereto; and
obtain an NMT baseline based on the measured muscle responses.

* * * * *